United States Patent [19]

Wurzburg et al.

[11] 4,067,775

[45] Jan. 10, 1978

[54] PROCESS AND COMPOSITION FOR DETERMINING THE ACTIVITY OF CREATINEKINASE-MB

[75] Inventors: Uwe Wurzburg; Norbert Hennrich; Hans-Dieter Orth; Hermann Lang, all of Darmstadt, Germany

[73] Assignee: Merck Patent Gesellschaft mit beschrankter Haftung, Darmstadt, Germany

[21] Appl. No.: 737,587

[22] Filed: Nov. 1, 1976

[30] Foreign Application Priority Data

Nov. 3, 1975 Germany .............................. 2548963

[51] Int. Cl.[2] ...................... G01N 33/00; G01N 31/14
[52] U.S. Cl. ............................... 195/99; 195/103.5 A; 195/103.5 R; 424/12
[58] Field of Search ................. 195/103.5 R, 103.5 A, 195/99; 424/2, 8, 12

[56] References Cited

U.S. PATENT DOCUMENTS

3,932,221  1/1976  Pfleiderer .............................. 195/99
3,994,783  11/1976  Rao et al. ...................... 195/103.5 R

OTHER PUBLICATIONS

Wreton et al., Clinica Chimica Acta, 58(1975) pp. 223–232.
Samuels, Annals New York Academy of Sciences, vol. 103, pp. 858–889 (1963).

*Primary Examiner*—Alvin E. Tanenholtz
*Attorney, Agent, or Firm*—Millen & White

[57] ABSTRACT

A process for determination of CK-MB activity in a sample of a body fluid comprising the steps of incubating the sample, optionally in the presence of CK substrates, with antibodies which inhibit enzymatic activity of the M subunit in CK isoenzymes MM and MB without inactivating enzymatic activity of the B subunit in any CK-MB which may be present and determining the activity of the CK B subunit in the resultant sample.

23 Claims, No Drawings

PROCESS AND COMPOSITION FOR DETERMINING THE ACTIVITY OF CREATINEKINASE-MB

BACKGROUND OF THE INVENTION

The invention relates to a process and a composition for determining the activity of creatinekinase-MB in human body fluids.

The determination of the activity of creatinekinase (ATP: creatine-phosphotransferase, E.C. 2.7.3.2; abbreviation; CK) in serum is considered the most sensitive laboratory method for diagnosing diseases of skeletal muscles and the myocardium, especially myocardial infarction. However, differentiation between trauma of skeletal muscles and the myocardium is difficult, especially in making a differential diagnosis of myocardial infarction. Determination of total CK activity results in unreliable differentiation.

Prior attempts to improve the reliability of evidence provided by determination of CK activity in differential diagnosis have used measurements of activity of other enzymes in the serum and correlation of the resulting measurement with each other, for example, quotient CK/glutamic oxalacetic transaminase. However quotients of this type cannot be used to differentiate between cardiac infarction and pulmonary infarction or between cardiac infarction and secondary shock resulting from other causes.

CK occurs in the body in the form of three isoenzymes, namely CK-MM, for example, in muscles; CK-BB, for example, in the brain; and hybrid CK-MB, consisting of an M and a B subunit, for example, in the myocardium. CK activity in blood serum is normally due to the CK-MM isoenzyme, because CK-BB does not pass through the fluid-blood barrier and CK-MB is restricted to certain organs, for example, the myocardium. However, when the myocardium is damaged, as in cardiac infarction, CK-MB is released into the blood serum and can be detected there.

Quantitative determination of this isoenzyme along with CK-MM in the serum is considered the most sensitive laboratory method and provides the greatest evidence in differential diagnosis of cardiac infarction. It is true that CK-MB is present in other organs, for example, the pancreas, the diaphragm, the aorta, the lungs and the uterus, as well as in the myocardium but the activity thereof in these organs is about 100 times less than in the myocardium, so that any CK-MB activity liberated from these other organs is below the limits of detection.

Determination of CK-MB activity previously was based essentially on one of three methods:

1. Electrophoresis on various carriers. The results obtained by this method are sometimes contradictory. Frequently the number of bands appearing is greater than the number of isoenzymes present, that is, artifacts cause unreliability.

2. Column chromatography on various materials. This method is time-consuming, has an actual operating time of several hours and is therefore not suitable for routine investigations. Results obtained by different investigators are sometimes contradictory.

3. Immunological determination by antibodies causing precipitation. This method, described in German Pat. Application Nos. P 21 28 670, (U.S. Pat. No. 3,932,221), and P 22 58 822, (U.S. Ser. No. 419,283, filed Nov. 27, 1973) gives good results, for example, in the quantitative determination of aldolase and alkaline phosphatase isoenzymes. However, the sensitivity of the method is inadequate for determination of relatively low activities of CK and especially of CK-MB.

In the processes described in German Pat. applications Nos. P 21 28 670 and P 22 58 822, the isoenzymes of CK are precipitated by antibodies which effect precipitation and act specifically on isoenzymes. In each case the residual activity in the supernatant liquor from the immune precipitation is determined. Apart from the effort involved in this method, which as a rule necessitates the preparation of several specific antisera, it is necessary to carry out at least two different tests, that is, determination of total CK activity and determination of residual CK activity after precipitation. Thus, the CK-MB activity can be determined only by measuring a difference. The result is therefore subject, in accordance with the rules of the theory of errors, to the uncertainty of both measurements. In the method of the invention, the addition of errors is avoided by making a direct measurement.

Another disadvantage of the precipitation process is that the immune precipitation, which is a secondary reaction, takes from about 60 minutes to several hours, so that the process is not suitable as a rapid test.

Owing to the relatively long time required to carry out all of the above processes, they are not suitable for rapid diagnosis of cardiac infarction.

Thus, there is a continuing need for a simple, rapid and reproducible process and composition for determining the activity of CK-MB in a sample of a body fluid.

This object is achieved according to the invention by a process which operates by using specific antibodies to completely inhibit enzymatic activity of the M subunit in CK-MM and CK-MB without inactivating enzymatic activity of the B subunit in any CK-MB which may be present.

SUMMARY OF THE INVENTION

In a method-of-use aspect, this invention relates to a method for determining the enzymatic activity of creatinekinase-MB in a biological sample, which comprises the steps of:

a. incubating the creatinekinase-containing sample with antibodies which completely inhibit the enzymatic activity of the M subunit of creatinekinase (CK) isoenzymes MB and MM but which do not inhibit the enzymatic activity of the B subunit of any creatinekinase-MB which may be present in the sample to immunologically inhibit the M subunit thereof, wherein complete inhibition of said enzymatic activity of said M subunit leaves less than 5 U./l. of said enzymatic activity intact and non-inhibition of said enzymatic activity of said B subunit is less than 10 U./l.; and (b) determining the enzymatic activity of the creatinekinase B subunit in the resultant sample.

In a compositional aspect, this invention relates to a composition for determining the activity of creatinekinase-MB by the above method in a biological sample comprising antibodies being substantially free of CK-BB isoenzyme activity and being able to inhibit completely the enzymatic activity of the M subunit of creatinekinases MM and MB without inactivating the the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l.

In another compositional aspect, this invention relates to a composition for determining the activity of creatinekinase-MB by the above method in a biological sample comprising a. anti-skeletal muscle CK-MM antibodies being substantially free of CK-BB isoenzyme activity and being able to inhibit completely the enzymatic activity of the M subunit of creatinkinases MM and MB without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l., and b. an enzyme-coenzyme/substrate mixture containing hexokinase, glucose-6-phosphate-dehydrogenase, adenosine diphosphate, nicotinamide-adenine-dinucleotide-phosphate, creatine phosphate and glucose.

In another aspect this invention relates to a test kit utilizing (a) the above composition and (b) an enzyme-coenzyme/substrate mixture containing hexokinase, glucose-6-phosphate-dehydrogenase, adenosine diphosphate, nicotinamide-adenine-dinucleotide-phosphate, creatine phosphate and glucose.

In another method of use aspect, this invention relates, in a method of diagnosing myocardial infarction by determining the concentration of creatinekinase isoenzymes in a sample of a body fluid, to the improvement of determining CK-MB activity by the above process.

DETAILED DESCRIPTION

A suitable body fluid for the process of the invention is human serum. It is also possible to use biological liquids, e.g., whole blood, plasma, lymph, urine, sputum and sweat of humans, or other animals, as well as enzyme preparations, for the determination. CK-BB interferes with the process of the invention and therefore must not be present in the biological fluids being tested.

Antibodies required for the process of the invention are obtained from animals inoculated with CK-MM antigens from skeletal muscle tissue. Human CK-MM is preferably used as antigen. CK-MM from animals can be used if the antisera are able to inhibit completely enzymatic activity of the M subunit in human CK-MM and CK-MB, if necessary, in the presence of CK substrates, without inactivating enzymatic activity of the B subunit in any CK-MB which is present. Animals donors of CK-MM antigens are, for example, various species of monkeys, preferably Rhesus monkeys and chimpanzees; domestic animals, such as pigs, horses, cattle, rabbits and guinea-pigs; and other animals, e.g., rats and mice and birds, such as geese, ducks and hens.

The CK-MM antigen used to produce the antibodies should be free from CK-MB and CK-BB activity. A sensitive criterion of this purity requirement is immunological analysis advantageously carried out by diffusion or electrophoresis techniques. In addition, analytical disc electrophoresis and polyacrylamide-gel electrofocussing are useful. Purity with respect to CK-MB and CK-BB takes precedence over absolute purity with respect to other proteins, which, for example, can be determined by the two latter methods. Microheterogeneity of types of CK-isoenzymes manifested, for example, in slight differences in amino acid composition of the individual isoenzymes, is as a rule of no importance as a criterion of purity.

Animals used for the immunization are those which, after inoculation with activated CK-MM, form antibodies which are able completely to inhibit enzymatic activity of the M subunit in the creatinekinases MM and MB without inactivating the enzymatic activity of the B subunit in CK-MB. Goats are preferred, particularly for production of antibodies able to effect complete inhibition of the M subunit in CK-MM and CK-MB, even in the presence of CK substrates. However, other animals, especially vertebrates, can also be used as antibody donors, for example, species of monkeys, horses, cattle and cattle-like animals, sheep, dogs, pigs, rabbits, birds, such as hens, turkeys, geese and ducks, and also rats, mice and guinea-pigs.

Immunization of the test animals is carried out with activated human or animal CK-MM. Activation of CK-MM can be effected by known reagents which stabilize and activate SH groups and/or by divalent metal ions, preferably by a combination of reagents and metal ions. Examples of preferred reagents which stabilize and activate SH groups are N-acetylcysteine, mercaptoethanol and dithioerythritol, as well as glutathione, cysteine, dithiothreitol, S-(2-aminoethyl)-isothiouronium bromide hydrobromide (AET) and/or thioglycollic acid.

Divalent metal ions orginate from corresponding water-soluble salts, for example, chlorides or acetates, preferably of magnesium as well as manganese, calcium and/or cobalt. Activators of this type are known in principle in other fields and those skilled in the art are conversant with them.

Subsequent immunization and separation to obtain antisera or antibodies are carried out in a known manner. The processing and storage of the antisera or antibodies is also carried out by methods known in immunology.

Antibodies used for the process of the invention are preferably of the IgG immune globulin (bivalent antibodies) category. Their molecular weight is between about 130,000 and 210,000, preferably about 160,000. The approximate sedimentation constant is between 6 S and 8 S, preferably about 7 S, as determined by analytical ultracentrifugation. Their carbohydrate content is about 3% of total weight, determined by the methods described in "Handbook of Experimental Immunology" ed. by D. M. Weir, 2nd edition 1973, pages 10.45 – 10.58, Blackwell Scientific Publications. Monovalent IgG fragments ($=F_{ab}$) and IgM antibodies can also be used according to the invention.

The antibodies used should completely inhibit enzyme activity of M subunit of creatinekinase. In this context, "complete inhibition" means inhibition with which, on an average, at most 5 U./l. and preferably less than 3 U./l. of the enzyme activity of the M subunit in CK-MM and CK-MB remain intact in a sample, as determined by conventional enzyme activity tests.

An agent for determining activity of CK-MB in a sample of a body fluid contains antibodies which are able to inhibit completely enzymatic activity of the M subunit in creatinekinases MM and MB without inactivating enzymatic activity of the B subunit in any CK-MB which may be present. In a preferred embodiment of this agent, the antibodies contained therein are able completely to inhibit up to 2,500 U./l. of the M subunit in CK-MM and CK-MB in the sample being analyzed.

This agent is used for determination of activity of CK-MB along with CK-MM, particularly as an aid in diagnosis of myocardial infarction and/or other diseases of, or damage to, the myocardium. A further subject of the invention is use of this agent for simultaneous determination of total CK activity and CK-MB activity in a sample.

The antibodies should have no effect on enzymatic activity of the B subunit in CK-MB. In this context, this means that at most 10 U./l., and preferably less than 5 U./l., of the enzyme activity of the B subunit in CK-MB are inhibited in a sample, as determined by conventional enzyme activity tests.

In a preferred embodiment of the process, in which the sample of body fluid being analyzed and the antibodies are incubated in the presence of CK substrates, the antibodies should be able to develop their inhibitory action against the enzymatic activity of the M subunit in CK-MM and CK-MB to the maximum, even in the presence of CK substrates, without influencing enzymatic activity of the B subunit in CK-MB. This property is present, in addition to properties characterized above, in, for example, antibodies which are obtained from goats by immunization with fully activated CK-MM. This requirement is not absolutely essential in carrying out the process according to the invention in the normal manner by first incubating with antibodies and then adding the CK substrate and measuring the residual activity of CK in the resultant sample.

CK substrates which can be employed are the substrates and effectors customarily used. Creatine or creatine phosphate, respectively, adenosine triphosphate or adenosine diphosphate, respectively, and magnesium ions are preferred.

Determination of the activity or the residual activity of CK and of its isoenzymes can be carried out by any processes which are rapid and precise, for example, photometry. This is carried out after auxiliary reactions.

It is also possible to use colorimetric methods, as described, for example, in "Methoden der enzymatischen Analyse", edited by H. U. Bergmeyer, 3rd edition (1974), Volume 1, page 145 et seq. Kinetic methods in which enzyme activity is determined by measurement in UV at, for example, 334, 340 or 366 nm are preferred for this purpose. Especially preferred is a standard method in which CK is determined using creatine phosphate and adenosine diphosphate, Z. Klin. Chem. Klin. Biochem., Volume 8, page 658 et seq. (1970) and Volume 10, page 182 (1972). Test packs for determining CK activity by this method are available commercially.

CK can also be determined fluorometrically. Creatine is liberated from creatine phosphate by CK and this creatine can be measured fluorometrically in a process developed by R. B. Conn, Clin. Chem., Volume 6, page 537 et seq. (1960), by reaction with ninhydrin in a strongly alkaline solution. See also, Sax et al, Clin. Chem., Volume 11, page 951 et seq. (1965).

In a typical embodiment of the process of the invention, CK-MM antibodies are added to a sample of body fluid being analyzed, preferably a sample of human serum, in an amount sufficient to inhibit completely up to 2,500 U./l., preferably about 1,000 U./l., of the M subunit in CK-MM and CK-MB. With body fluids having higher total CK activities, preliminary dilution to about 1,000 U./l. is appropriately carried out before actual determination and taken into account in the calculations. The mixture thus prepared is incubated for about 1 to 30, preferably about 5, minutes at temperatures between +10° and +40° C., preferably at about room temperature, most preferably, 25° or 30° C. Residual enzyme activity of the reaction mixture is then determined by a known process, preferably the UV method described above.

The serum/antibody mixture is then added to a known enzyme-coenzyme/substrate mixture containing all the enzymes, coenzymes and substrates necessary for carrying out the method and an adequate amount of a buffer solution, pH about 7, is then added. Customary commercially available formulations contain, for example, hexokinase, glucose-6-phosphate-dehydrogenase, adenosine diphosphate and nicotinamide-adenine-dinucleotide-phosphate as the enzyme-coenzyme mixture and creatine phosphate and glucose as substrates.

The serum/antibody mixture can be added to a mixture of the coenzyme and the enzyme, or vice versa, and then a buffer/substrate mixture can be added. Buffers which are suitable for the reaction are neutral buffers, for example, triethanolamine, imidazole acetate, morpholinepropanesulfonic acid and morpholineethanesulfonic acid buffers. Triethanolamine and imidazole acetate buffers are preferred.

The mixture is prepared and incubated for about 1 to 10, preferably 5, minutes at 15° – 40°, preferably at 25° or 30° C. and the change in extinction is determined at about room temperature. The activity of the subunit B in CK-MB is calculated.

In a preferred embodiment, a sample of the biological fluid being analyzed is incubated together with antibodies and CK substrates in the presence of a buffer and the substances required for the identification reaction without previous incubation of the sample with the antibodies.

In this embodiment, the antibodies used must completely inhibit enzymatic activity of the M subunit in CK-MM and CK-MB even in the presence of CK substrates. Antibodies having this property are, for example, obtained from goats using fully activated CK-MM. The antibodies enable the process of the invention to be carried out in a simple and rapid manner.

For example, antibodies previously lyophilized with the known coenzyme/enzyme/substrate mixture used for the identification reaction are dissolved in a selected amount of buffer solution. Body fluid, for example, serum, being analyzed is added and determination of the activity of the B content of CK-MB is made. In a variation of this process, the antibodies are incorporated into the lyophilizate with a mixture consisting only of coenzymes and enzymes. The substrates are then added to the buffer solution.

In a further preferred embodiment, simultaneous determination of total CK activity and of CK-MB activity can be carried out in a single batch by the preferred process just described. Thus, 1. total CK activity of the sample is first determined by a known photometric process;
2. a lyophilizate consisting of CK-MM antibodies is dissolved in water and added to the same batch;
3. The mixture is then incubated at 2 to 40, preferably 25° to 37° C. for about 1 to 10, preferably 5, minutes and residual activity of the sample is determined photometrically.

In this embodiment, the CK-MM antibodies must completely inhibit enzymatic activity of the M subunit in CK-MM and CK-MB, even in the presence of CK substrates.

In this preferred embodiment, antibody capacity of the antisera can be adjusted so as to completely inhibit up to 2,500 U./l., preferably about 1,000 U./l., of the M subunit in CK-MM and CK-MB. If total CK activities of the sample being analyzed are too high for this inhibitory capacity of the antibodies, preliminary dilutions must be carried out, for example, to activities of M subunit in CK-MM and CK-MB of about 1,000 U./l.

In a most preferred embodiment, the method of this invention is the foregoing, wherein said biological fluid is blood serum and the blood serum and antibodies are incubated in the presence of a CK substrate; including a preliminary step, prior to incubation of said sample with said antibodies, of determining total CK activity in said sample; complete inhibition of said enzymatic activity of said M subunit leaves less than 3 U./l. of said enzymatic activity intact and non-inhibition of said enzymatic activity of said B subunit is inhibition of less than 5 U./l.; said antibodies are anti skeletal muscle CK-MM from goats; and said antibodies are able to inhibit completely up to 2,500 U./l. of M subunit of creatinekinases MM and MB in said sample.

In a most preferred embodiment, the preferred method above is used to determine CK-B isoenzyme activity in an improved method of diagnosing myocardial infarction.

In a most preferred embodiment, the composition of this invention is one wherein said antibodies are able to effect complete inhibition of said enzymatic activity of said M subunit in CK-MM and CK-MB without inhibiting said enzymatic activity of said B subunit, even in the presence of CK substrates; and said antibodies are antiskeletal muscle CK-MM obtained from goats.

In a preferred embodiment, the test kit of this invention is one in which (b) the CK substrate comprises disodium creatine phosphate hexahydrate, reduced glutathione or N-acetylcysteine, disodium adenosine diphosphate hexahydrate, disodium nicotinamideadenine dinucleotide phosphate, disodium adenosine monophosphate, hexokinase, glucose-6-phosphate dehydrogenase, glucose and magnesium acetate; and said kit further contains (c) a buffer solution of triethanolamine or imidazole acetate.

The process of the invention has several advantages over known art, including highly precise results and the rapidity and simplicity with which the process is carried out.

The precision of the process of the invention is thought to be due to the use of antibodies which act specifically on the M subunit of CK-MM and CK-MB and therefore enable the CK-MB activity in body fluids, such as human serum, to be determined directly.

Inhibiting antibodies against CK isoenzymes have also been described in Clin. Chem. Acta, Volume 58, pages 223-232 (1975). In addition to a 100% inhibition of CK-MM, these antibodies also effect 80% inhibition of CK-MB. In addition to inhibition of the M subunit of CK-MB, a substantial proportion of the B subunit is also inhibited by the antibodies used, since the ratio of activity of each of the M and B subunits in CK-MB to total activity of this isoenzyme is approximately 50 : 100. Even if the residual activity of about 20%, determined using these antibodies were reproducible, the values obtained would nevertheless be too low to be detected reliably in an accurate measurement of CK-MB, owing to the already low total CK activity in serum. Accordingly, inhibiting antibodies described above have not been used to determine CK isoenzyme concentration by the inhibition principle. Using the process of this invention, about 50% of CK-MB activity, i.e., approximately the entire activity of the B subunit, remains available for measurement. This represents a considerable advance in the art.

Reference is made to the copending U.S. application of U. Wuerzburg et al., Ser. No. 737,264 filed on even date herewith, describing the preparation of anti-CK-MM, whose disclosure is incorporated by reference, and to the corresponding German Pat. application P 25 48 962, filed Nov. 3, 1975.

A particular advantage of the process of the invention is the speed with which the process can be carried out. This is especially true of the preferred embodiment, in which inhibition of M content of CK-MM and CK-MB and determination of residual activity are carried out simultaneously. In this embodiment, an exact test result for making a diagnosis can be available within 5 to 30 minutes, usually between 5 and 15 minutes at 2 to 40, preferably 25° to 37° C.

The simplicity with which the process can be carried out is also a noteworthy advantage. The test method can be carried out in larger institutes or hospitals, using customary mechanized equipment for determining enzyme activities, or in smaller institutes or in a doctor's laboratory using a photometer.

Test packs containing all of the reagents necessary for carrying out the process of the invention, that is, a conventional mixture of coenzyme, enzyme and substrate, CK-MM antibodies of the invention and buffer solution, are suitable for individual determinations. A test pack of this type makes it possible to determine CK-MB with minimal effort.

It was unexpected that the problem of determining CK-MB by a process operating as simply and rapidly as the process of the invention, could be solved. The production of specific antisera which, while completely inhibiting enzymatic activity of the M subunit in CK-MM and CK-MB, do not affect enzymatic activity of the B subunit of CK-MB could not be foreseen. The availability of antibodies which have these properties makes the reaction according to the invention possible.

It is also surprising that the antibodies employed according to the invention retain full inhibitory power even in the presence of substrates. This is not to be expected. Antibodies which do not effect 100% inactivation of CK-MM in the presence of CK substrates have been described in the literature, Ann. N.Y. Acad. Sci., Volume 103, pages 858-889 (1963). Antibodies of this type would be completely useless in the preferred embodiments of the process of the invention, in accordance with which inhibition by antibodies and addition of CK substrates takes place simultaneously. Uninhibited proportions of the M activities would falsely increase the measured value for CK-MB and in some cases would simulate CK-MB activity which was not present at all. In this way, false laboratory data for the diagnosis would result.

Determination of CK-MB activity with a rapidity and precision not achievable hitherto with immunological methods is made possible by the surprising property of the antibodies employed according to the invention, that is, complete inhibition of enzymatic activity of the M subunit of CK-MM and CK-MB without affecting enzymatic activity of the B subunit of CK-MB and, at the same time, of completely developing their inhibitory power with respect to the M subunit and CK-MM and CK-MB in the presence of substrates. This permits practical determination of CK-MB activity by a rapid test.

It becomes possible, from laboratory findings of an increase in CK-MB activity in a patient, to differentiate between a disease or traumatism of skeletal muscles and of the myocardium. Owing to release of CK-MB into the blood stream and other body fluids following trauma to the myocardium, it is apparent that CK-MB isoenzyme activity is an extremely reliable indication of whether myocardial damage has occurred and that a differential diagnosis of myocardial damage can be made on the basis of elevation of CK-MB levels in the body fluids. This gives important additional data for differing cardiac infarction from pulmonary infarction and/or from secondary shock and other diseases of, or damage to, the heart.

Specific and exact determination of activity of CK-MB gives data on the extent to which the myocardium is involved in, or damaged by, other extracardiac disease processes, for example, poisoning or accidents; therapeutic intervention, for example, resuscitation; or diagnostic operations, for example, cardiac catheterization or coronary angiographs.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the examples which follow "M" (and "mM") are the concentrations in moles and millimoles, respectively, per liter.

PREPARATION OF STARTING MATERIALS

EXAMPLE A

Preparation of CK-MM a. 1.2 kg. of deep frozen human skeletal muscle are thawed at room temperature and broken up by machine. The tissue is suspended in 2.5 l. of cold 0.05 M tris/ Cl buffer of pH 8.0 (tris-(hydroxymethyl)-aminomethane/HCl buffer) which contains 0.01 M. of KCl, 1 mM of EDTA (ethylenediaminetetraacetic acid) and 1 mM of dithioerythritol and the suspension is homogenized with a mixer. The homogenized material is stirred for 45 minutes while being cooled with ice and is then centrifuged at 12,000 g for 60 minutes. The clear supernatant liquor (2.680 l.) is subjected to ammonium sulfate fractionation at pH 8.0 between limits of 40 – 75% saturation. The 0.75 s-precipitate is taken up in 0.04 M tris/HCl buffer at pH 8.0 and dialyzed against the same buffer. In order to adsorb myoglobin and acid ballast proteins, 500 g. of a moist basic ion exchanger resin derived from crosslinked dextran and equilibrated against the same buffer are added. After 30 minutes, the exchange resin is filtered off and washed twice with 400 ml. of 0.04 M tris/HCl buffer containing 0.02 M of NaCl at pH 8.0. The filtrate and wash water are combined and brought to 0.75 s with ammonium sulfate. The precipitate is centrifuged off, dissolved in 100 ml. of 0.04 M tris/HCl buffer at pH 8.0 and dialyzed against the same buffer until no further ammonium sulfate can be detected. The clear dialyzate is equilibrated on a column packed with a basic ion exchange resin derived from a crosslinked dextran (6 × 60 cm.) using the same buffer. The column is washed with the initial buffer until the eluate is protein-free. The enzyme is then eluted from the column with 0.04 M tris/HCl buffer containing 0.02 M of NaCl, 1 mM of EDTA and 1 mM of dithioerythritol at pH 8.0. Fractions having an enzyme content of at least 20 U./ml. are combined and 80%-saturated with ammonium sulfate and the precipitated enzyme is centrifuged down. For final purification, the enzyme is again subjected to chromatography in the same system, using a smaller volume in the column. The enzyme is precipitated from the combined active fractions with 0.8 s-ammonium sulfate and dissolved in 50 ml. of 0.04 M tris/HCl buffer containing 0.02 M of NaCl, 1 mM of EDTA and 1mM of dithioerythritol at pH 8.0, to give a concentrated solution. The latter is filtered under sterile conditions and again brought to 0.8 s with ammonium sulfate. In this way, an enzyme suspension, which is stable at 4° C., of CK-MM with a specific activity of 26-30 U./mg., measured with creatine as substrate at 25° C., is obtained.

Volume: 86 ml.; activity: 316 U./ml.; protein: 11.8 mg./ml.; Yield: about 30%, based on organ extract.

b. Analogously to Example (Aa), CK-MM is isolated from muscle tissue from the following animals: Rhesus monkeys, pigs and cattle.

EXAMPLE B

Preparation of anti-CK-MM.

a. CK-MM from human muscle is dialyzed against a physiological NaCl solution buffered with 0.07 M of triethanolamine, containing 10 mM of mercaptoethanol and 10 mM of $MgCl_2$ at pH 7.0. The enzyme solution is freed from aggregates by ultracentrifugation and the protein content is adjusted to 2 mg./ml. using the dialysis buffer. 1 ml. of this solution is emulsified with 1 ml. of complete Freund's adjuvant, a water/mineral oil suspension additionally containing 2 mg. of destroyed M-turberculosis bacillae. This emulsion is injected intramuscularly into a goat. Three injections of the same type at intervals of 3 weeks and 3 further booster injections, each at intervals of 16 weeks, are made. Blood is taken from the animal 21 days after the last injection. The pH of the serum, obtained by known methods, is adjusted to 8.4 using a mixture containing 3% sheep serum albumin and 0.1% of sodium azide in 0.1 M borate buffer and the serum is filtered under sterile conditions. The resulting solution, which contains anti-human muscle CK-MM, is charged in 0.5 ml. portions to brown glass bottles and freeze-dried. The antibodies have a molecular weight of about 160,000 to 180,000.

b. CK-MM from human muscle obtained according to Example (Aa) is dialyzed against physiological NaCl solution, buffered with 0.1 M of imidazole at pH 6.8 and containing 7.5 mM of N-acetyl-cysteine and 25 mM of magnesium acetate. The enzyme solution is then freed of aggregates by ultracentrifugation and the protein content is adjusted to 0.2 mg./ml. with the dialysis buffer. 1 ml. of this solution is emulsifed with 1 ml. of complete Freund's adjuvant. This emulsion is injected intradermally into a wether. This injection is followed by 2 intramuscular injections after 3 and 6 weeks and 3 further booster injections, each at intervals of 14 weeks. Blood is taken 19 days after the last injection. The work up is analogous to Example (Ba). Anti-human muscle CK-MM is obtained in freeze-dried form. The mulecular weight of the antibodies is about 160,000 to 180,000.

c. CK-MM from Rhesus monkey muscle is thoroughly dialyzed against physiological NaCl solution buffered with 0.15 M of imidazole, and containing 25 mM of dithioerythritol and 15 mM of manganese-II chloride at pH 6.8. After aggregates have been removed by ultracentrifugation, the protein content is adjusted to 5 mg./ml. with the dialysis buffer. 1 ml. of this solution is emulsified with 1 ml. of complete Freund's adjuvant. Injections, withdrawal of blood and the work up are carried out as in Example (Ba). Anti-Rhesus monkey muscle CK-MM is obtained in freeze-dried form. The sedimentation constant of the antibodies is about 7S.

d. CK-MM from pig muscle is activated as in Example (Bb) and the antigen emulsion with complete Freund's adjuvant is injected into rabbits. Another subcutaneous antigen injection is made after 3 weeks. The injection is repeated after 3 weeks more and blood is taken 19 days after this injection. Isolation is carried out as in Example (Ba). Anti-pig muscle CK-MM is obtained in freeze-dried form. The molecular weight of the antibodies is about 160,000 to 180,000.

e. Anti-cattle muscle CK-MM (molecular weight about 160,000 to 180,000) is obtained from cattle muscle in an analogous manner.

EXAMPLE 1

Inhibition of CK-MM, CK-MB and CK-BB by anti-human-CK-MM

Pure CK-MM, CK-MB or CK-BB is added to human serum inactivated in respect of its own CK activity and CK activities of individual samples are determined. 0.1 ml. of anti-CK-MM solution, obtained according to Example Ba, is then added to 0.1 ml. of a sample and the two are mixed and incubated for 5 minutes at 25° C. Residual CK activity is then determined in a known way. Results are given in the table:

TABLE

Residual activities of CK isoenzymes after incubation with inhibiting anti-human-CK-MM (average values ± 1 s obtained from 5 determinations in each case) (s= standard deviation)

| Isoenzyme | Activity of the isoenzymes added (U./l.) | Residual activity after incubation with anti-CK-MM (U./l.) |
|---|---|---|
| CK-MM | 98 ± 1.9 | 0.3 ± 2.1 |
|  | 1043 ± 22 | 0.5 ± 2.5 |
| CK-MB | 103 ± 2.0 | 53 ± 1.7 |
|  | 410 ± 7.8 | 206 ± 6.2 |
| CK-BB | 197 ± 3.8 | 199 ± 4.1 |

Within errors of measurement, inhibition of activity is 100% for CK-MM, 0% for CK-BB and 50% for CK-MB, corresponding to the content of 50% of M subunits. Results are constant over a wide range of activities of isoenzymes added.

EXAMPLE 2

Test I for quantitative determination of activity of CK-MB in body fluids a. Composition of the test pack:

The test pack is sufficient for 10 activity determinations. The pack contains 1 bottle of buffer sufficient for 10 determinations, 10 bottles of coenzyme/enzyme/substrate mixture and 1 bottle of anti-CK-MM, obtained according to Example (Ba).

The bottle of coenzyme/enzyme/substrate mixture contains:

| | |
|---|---|
| disodium creatine phosphate hexahydrate | 27.24 mg. |
| reduced glutathione | 6.4 mg. |
| or N-acetyl cysteine | 3.4 mg. |
| disodium adenosine diphosphate hexahydrate | 1.25 mg. |
| disodium nicotinamide adenine dinucleotide phosphate | 1.7 mg. |
| disodium adenosine monophosphate | 8.47 mg. |

-continued

| | | |
|---|---|---|
| hexokinase | 5 | U. |
| glucose-6-phosphate dehydrogenase | 3 | U. |
| glucose | 8.32 | mg. |
| magnesium acetate | 4.52 | mg. |

The bottle of buffer solution contains: triethanolamine acetate (in water) 105 mM The lyophilized antibodies are dissolved in 2 ml. of distilled water. The resulting antibody solution is adjusted so that it totally inhibits up to 1,000 U./l. of creatinekinaseMM. Sera having extremely high total creatinkinase activities must therefore be diluted previously to about 1,000 U./l. The antibody solution is stable for at least 7 days at +4° C.

b. Method for determining the activity of CK-MB:

b. Method:

Pipette 0.1 ml. of serum and 0.1 ml. of antibody solution into a reaction vessel. Mix well and incubate for 5 minutes at 25° C. 0.1 ml. of this reaction mixture and 2.0 ml. of buffer solution are then transferred to a bottle containing the mixture of coenzyme, enzyme and substrate.

Mix and incubate for 5 minutes at 25° C., then pour into a cuvette and measure the extinction at 25° C. and then determine the change in extinction per minute. Wavelength: 334, 340, or 336 nm; layer thickness: 1 cm.

b2. Calculations:

The CK activity determined for the sample must be multiplied (a) by the dilution factor 2 and (b) by the CK-MB hybrid factor 2, since only the B subunits of CK-MB are measured in the test.

An average value is obtained from the difference in extinction per minute ($\Delta E$/minute) and this is used in the appropriate formula for calculation:

Measurement at 334 nm: activity of CK-MB per unit volume = $\Delta E$/minute $\times$ 4 $\times$ 3,500 U./l.

Measurement at 340 nm: activity of CK-MB per unit volume = $\Delta E$/minute $\times$ 4 $\times$ 3,376 l U./l.

Measurement at 366 nm: activity of CK-MB per unit volume = $\Delta E$/minute $\times$ 4 $\times$ 6,364 U./l.

*Compare "Methoden der enzymatischen Analyse," edited by H. U. Bergmeyer, 3rd edition (1974), page 331 et seq.

EXAMPLE 3

Test II for quantitative determination of activity of CK-MB in body fluids a. Composition of the test pack:

The test pack is sufficient for 30 activity determinations. The pack contains 1 bottle of buffer solution for 30 determinations and 30 bottles of a lyophilized mixture consisting of coenzyme, enzyme, substrate and anti-CK-MM of Example (Ba).

The amount of triethanolamine acetate in the bottle of buffer solution corresponds to the amount of Example 2a. The composition of the mixture of coenzyme, enzyme, substrate and anti-CK-MM of Example (Ba) in the individual bottles corresponds to that in Example 2a with respect to the three first-mentioned components and each bottle additionally contains anti-CK-MM which totally inhibits up to 1,000 U./l. of CK-MM.

b. Determination of the activity of CK-MB b1. Method 2.0 ml. of buffer solution and 0.1 ml. of serum are pipetted into the contents of a bottle of coenzyme/enzyme/substrate/anti-CK-MM mixture. Mix and incubate for 5 minutes at 25° C. Then pour into a cuvette and measure the extinctions at 25° C. over a period of 5 minutes. Wavelength: 334, 340, 366 nm.; layer thickness: 1 cm.

b2. Calculation

An average value is obtained from the difference in extinction per minute (E/minute) and this is used in the appropriate formula for calculation:
Measurement at 334 nm: activity of CK-MB per unit volume = $\Delta E/\text{minute} \times 7{,}000$ 1 U./l.
Measurement at 340 nm: activity of CK-MB per unit volume = $\Delta E/\text{minute} \times 6{,}752$ U./l.
Measurement at 366 nm: activity of CK-MB per unit volume = $\Delta E/\text{minute} \times 12{,}728$ U./l.

EXAMPLE 4

Simultaneous determination of the total CK activity and of the CK-MB activity a. Composition of the test pack:

The composition of the test pack corresponds to that of Example 2a.

b. Determination of total CK activity and of CK-MB activity of CK-MB.

b1. Method:

2.0 ml. of buffer solution and 0.1 ml. of serum or diluted serum are pipetted into a bottle of coenzyme/enzyme/substrate mixture. Mix and incubate for 5 minutes at 25° C., then pour into a cuvette and determine the change in extinction ($\Delta E1$) at 25° C. over a period of 2 minutes. 0.1 ml. of antibody solution is then added. Mixing is carried out at once and after 3 minutes the change in extinction ($\Delta E2$) at 25° C. is again determined. Wavelength: 334, 340, 336 nm: layer thickness: 1 cm.

b2. Calculation:

The total CK activity is calculated as follows: Measurement at 334 nm: total activity of CK per unit volume = $\Delta E1/\text{minute} \times 3{,}500$ U./l.
Measurement at 340 nm: total activity of CK per unit volume = $\Delta E1/\text{minute} \times 3{,}376$ U./l.
Measurement at 366 nm: total activity of CK per unit volume = $\Delta E1/\text{minute} \times 6{,}364$ U./l.

The activity of CK-MB is obtained using the following formulae for calculation.
Measurement at 334 nm: activity of CK-MB unit volume = $\Delta E2/\text{minute} \times 7{,}350$ U./l.
Measurement at 340 nm: activity of CK-MB per unit volume = $\Delta E2/\text{minute} \times 7{,}090$ U./l.
Measurement at 366 nm: activity of CK-MB per unit volume = $\Delta E2/\text{minute} \times 13{,}364$ U./l.

EXAMPLE 5

Determination of CK-MB activities in patients with and without cardiac infarction using the test pack of Example 3

(a) CK activities in different groups of patients:

|  | Number of cases | Average values Total CK (U./l.) | CK-MB (U./l.) |
|---|---|---|---|
| Patients with increased CK activities without cardiac infarction | 48 | 480 | <1.7 |
| Patients with cardiac infarctions | 5 | 510 | 44 |

The tables shows that an indication of a cardiac infarction can be obtained rapidly and clearly with the method of determination of the invention. b. Change in CK-MB activities in a patient with cardiac infarction:

| Hours after the onset of infarction | CK-MB U./l. |
|---|---|
| 3.5 | <5 |
| 4.5 | <5 |
| 5.5 | 6 |
| 7.5 | 22 |
| 8.5 | 23 |
| 9.5 | 29 |
| 10.5 | 50 |
| 11.5 | 46 |
| 13.5 | 56 |
| 15.5 | 55 |
| 17.5 | 64 |
| 21.5 | 62 |
| 25.5 | 50 |
| 29.5 | 42 |
| 33.5 | 25 |
| 43.5 | 18 |
| 53.5 | <5 |
| 61.5 | <5 |

The figures show the rise and subsequent fall in CK-MB activity in a patient suffering from cardiac infarction determined by the process of the invention.

The preceding examples can be repeated with similar success by substituting the generically or specifically described reactants and/or operating conditions of this invention for those used in the preceding examples.

For the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for determining the enzymatic activity of creatinekinase-MB in a biological liquid sample, which comprises the steps of:
    a. incubating the creatinekinase-containing sample with antibodies which completely inhibit the enzymatic activity of the M subunit of creatinekinase (CK) isoenzymes MB and MM in solution without precipitation but which do not inhibit the enzymatic activity of the B subunit of any creatinekinase-MB which may be present in the sample to immunologically inhibit the M subunit thereof, wherein complete inhibition of said enzymatic activity of said M subunit leaves less than 5 U./l. of said enzymatic activity intact and non-inhibition of said enzymatic activity of said B subunit is less than 10 U./l.; and
    b. determining the enzymatic activity of creatinekinase B subunit in the resultant sample.

2. The method of claim 1, wherein said enzymatic activity is determined photometrically in step (b).

3. The method of claim 1, wherein the biological sample is blood serum and the blood serum and antibodies are incubated in the presence of a CK substrate.

4. The method of claim 1, further comprising a preliminary step, prior to incubation of said sample with said antibodies, of determining total CK activity in said sample.

5. The method of claim 4, wherein said complete inhibition of said enzymatic activity of said M subunit leaves less than 3 U./l. of said enzymatic activity intact and said non-inhibition of said enzymatic activity of said B subunit is inhibition of less than 5 U./l.

6. The method of claim 5, wherein said antibodies are anti-human skeletal muscle CK-MM, anti-Rhesus monkey skeletal muscle CK-MM, anti-pig skeletal muscle CK-MM, or anti-cattle skeletal muscle CK-MM.

7. The method of claim 5, wherein said antibodies are anti-human skeletal muscle CK-MM from goats.

8. The method of claim 1, wherein said antibodies are able to inhibit completely up to 2,500 U./l. of M subunit of creatinekinases MM and MB in said sample.

9. The method of claim 1, wherein said biological sample is blood serum and the blood serum and antibodies are incubated in the presence of a CK substrate; including a preliminary step, prior to incubation of said sample with said antibodies, of determining total CK activity in said sample; complete inhibition of said enzymatic activity of said M subunit leaves less than 3 U./l. of said enzymatic activity intact and non-inhibition of said enzymatic activity of said B subunit is inhibition of less than 5 U./l.; said antibodies are anti skeletal muscle CK-MM from goats; and said antibodies are able to inhibit completely up to 2,500 U./l. of M subunit of creatinekinases MM and MB in said sample.

10. A method according to claim 1, wherein said biological liquid sample is derived from a patient suspected of myocardial infraction.

11. A method according to claim 4, wherein said biological liquid sample is derived from a patient suspected of myocardial infraction.

12. A method according to claim 9, wherein said blood serum is derived from a patient suspected of a myocardial infraction.

13. A method according to claim 1, wherein said antibodies are substantially free of CK-BB isoenzyme activity and have a molecular weight of 130,000 – 210,000 and a sedimentation constant between 6 S and 8 S; and said antibodies are able to effect complete inhibition of said enzymatic activity of said M subunit in CK-MM and CK-MB without inhibiting said enzymatic activity of said B subunit, even in the presence of CK substrates.

14. A method according to claim 13, wherein the molecular weight is about 160,000 and the sedimentation constant is about 7 S.

15. A composition for determining the activity of creatinekinase-MB in a liquid biological sample comprising antibodies being substantially free of CK-BB isoenzyme activity and being able to inhibit completely the enzymatic activity of the M subunit of creatinekinases MM and MB in solution without precipitation and without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l., and an enzyme-coenzyme and substrate reagent for determining CK activity.

16. A composition for determining the activity of creatinekinase-MB in a liquid biological sample comprising a. antiskeletal muscle CK-MM antibodies being substantially free of CK-BB isoenzyme activity and being able to inhibit completely the enzymatic activity of the M subunit of creatinekinases MM and MB in solution without precipitation and without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l., and b. an enzyme-coenzyme and substrate mixture containing hexokinase, glucose-6-phosphate-dehydrogenase, adenosine diphosphate, nicotinamide-adenine-dinucleotidephosphate, creatine phosphate and glucose.

17. The composition of claim 15, wherein said antibodies are able to effect complete inhibition of said enzymatic activity of said M subunit in CK-MM and CK-MB without inhibiting said enzymatic activity of said B subunit, even in the presence of CK substrates.

18. The composition of claim 15, wherein said antibodies are anti-skeletal muscle CK-MM obtained by immunization of goats.

19. The composition of claim 15, wherein said antibodies are substantially free of CK-BB isoenzyme activity and have a molecular weight of 130,000 – 210,000 and a sedimentation constant between 6 S and 8 S; and said antibodies are able to effect complete inhibition of said enzymatic activity of said M subunit in CK-MM and CK-MB without inhibiting said enzymatic activity of said B subunit, even in the presence of CK substrates.

20. The composition of claim 19, wherein the molecular weight is about 160,000 and the sedimentation constant is about 7 S.

21. A test kit for the determination of the activity of creatinekinase-MB in a biological sample, which comprises:

a. antibodies being substantially free of CK-BB isoenzyme activity and being able to inhibit completely the enzymatic activity of the M subunit of creatinekinases MM and MB in solution without precipitation and without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l., and b. an enzyme-coenzyme and substrate reagent for determining CK activity.

22. A test kit for the determination of the activity of creatinekinase-MB in a biological sample, which comprises:

a. antibodies being substantially free of CK-BB isoenzyme activity and being able to inhibit completely the enzymatic activity of the M subunit of creatinekinases MM and MB in solution without precipitation and without inactivating the enzymatic activity of the B subunit of any creatinekinase-MB in the sample, wherein complete inhibition of said M subunit leaves less than 5 U./l. of said enzymatic activity intact and non-inhibition of said enzymatic activity of said B subunit is less than 10 U./l.;

b. an enzyme-coenzyme and substrate mixture comprising disodium creatine phosphate hexahydrate, reduced glutathione or N-acetylcysteine, disodium adenosine diphosphate hexahydrate, disodium nicotinamideadeninedinucleotide phosphate, disodium adenosine monophosphate, hexokinase, glucose-6-phosphatdehydrogenase, glucose and magnesium acetate; and c. a buffer solution of triethanolamine or imidazole acetate.

23. A kit according to claim 21, wherein said reagent contains hexokinase, glucose-6-phosphate-dehydrogenase, adenosine diphosphate, nicotinamide-adeninedinucleotidephosphate, creatine phosphate and glucose.

* * * * *